United States Patent [19]

Rhodes

[11] Patent Number: 5,122,154
[45] Date of Patent: Jun. 16, 1992

[54] ENDOVASCULAR BYPASS GRAFT

[76] Inventor: Valentine J. Rhodes, 608 Winding River Rd., Brick Town, N.J. 08723

[21] Appl. No.: 567,849

[22] Filed: Aug. 15, 1990

[51] Int. Cl.$^5$ .................. A61M 29/00; A61F 2/04
[52] U.S. Cl. ........................ 606/198; 623/1; 623/12
[58] Field of Search ........... 606/198, 153, 191, 194, 606/200, 108, 1; 623/1, 12; 604/96, 104

[56] References Cited

U.S. PATENT DOCUMENTS

| 3,657,744 | 4/1972 | Fursek | 606/153 |
|---|---|---|---|
| 4,047,252 | 9/1977 | Liebig et al. | 623/1 |
| 4,503,569 | 3/1985 | Dotter | 623/1 |
| 4,512,338 | 4/1985 | Balko et al. | 606/191 |
| 4,580,568 | 4/1986 | Gianturco | 606/198 |
| 4,655,771 | 4/1987 | Wallsten | 623/12 |
| 4,733,665 | 3/1988 | Palmaz | 606/191 |
| 4,740,207 | 4/1988 | Kregmer | 623/12 |
| 4,766,337 | 10/1988 | Palmaz | 606/108 |
| 4,795,458 | 1/1989 | Regan | 623/1 |
| 4,830,003 | 5/1989 | Wolff et al. | 623/1 |
| 4,856,516 | 8/1989 | Hillstead | 623/1 |
| 4,994,071 | 2/1991 | MacGregor | 606/194 |
| 5,035,706 | 7/1991 | Gianturco et al. | 606/198 |

Primary Examiner—C. Fred Rosenbaum
Assistant Examiner—William W. Lewis
Attorney, Agent, or Firm—Caesar, Rivise, Bernstein, Cohen & Pokotilow, Ltd.

[57] ABSTRACT

An intraluminal graft for placement in a blood vessel, duct, or lumen, to hold it open. The graft comprises a sleeve having plural stents thereon. The sleeve is an elongated tubular member formed of a conventional graft material which is flexible and impervious to the ingrowth of tissue therein. Each stent is a generally ring-like member formed a plurality of interconnected movable links and is mounted about the periphery of a surface, e.g., inner or outer, of the sleeve at selected points along the sleeve to form respective spaced first sleeve sections. Each of the first sections extends for only a portion of the length of the graft, thereby leaving a plurality of second sleeve sections interposed between the first sleeve sections. The stents and the sleeve are arranged to be expanded, e.g., by a balloon catheter, from a compact state to an expanded state to increase the inner cross sectional area diameter of the sleeve. In the expanded state the stents are resistant to contraction back to the compact state. The graft is able to bend with respect to its longitudinal axis to enable it to be readily accommodated within a curved blood vessel, duct, or lumen.

31 Claims, 4 Drawing Sheets

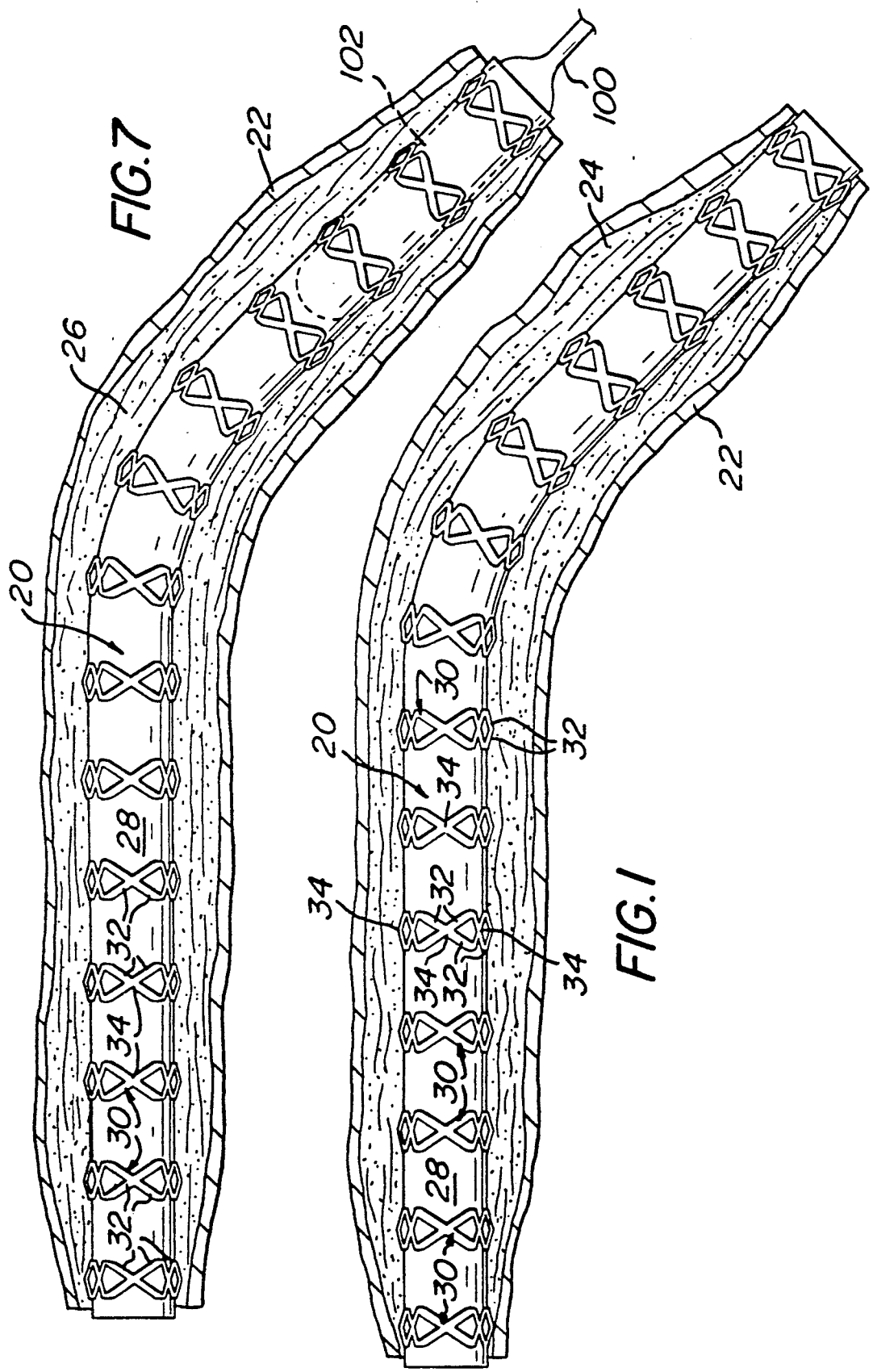

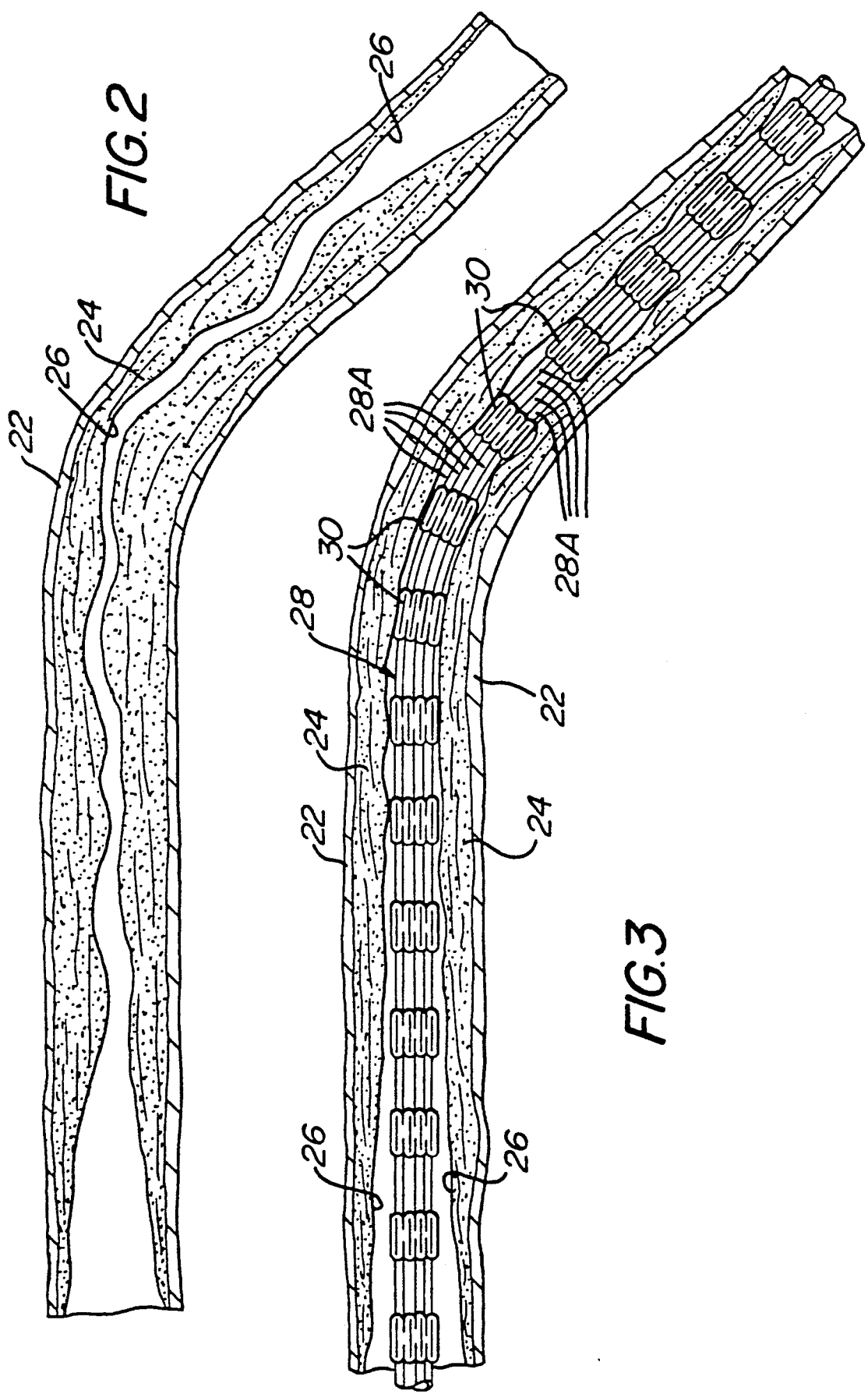

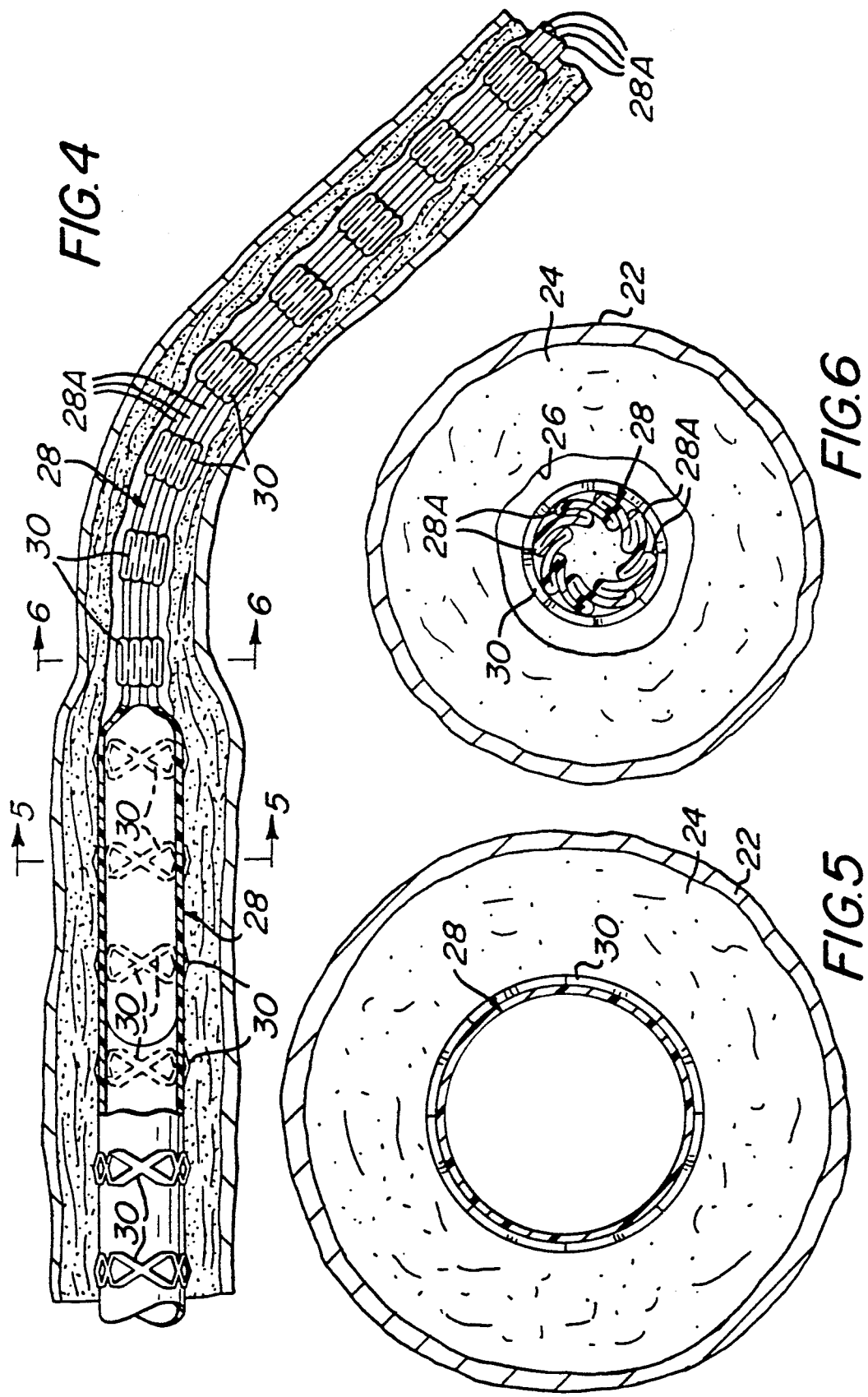

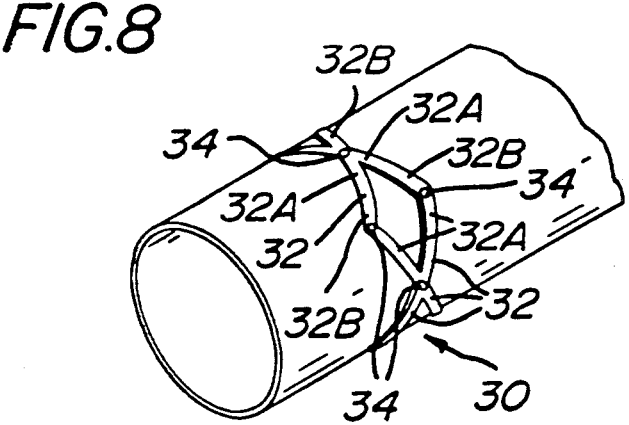
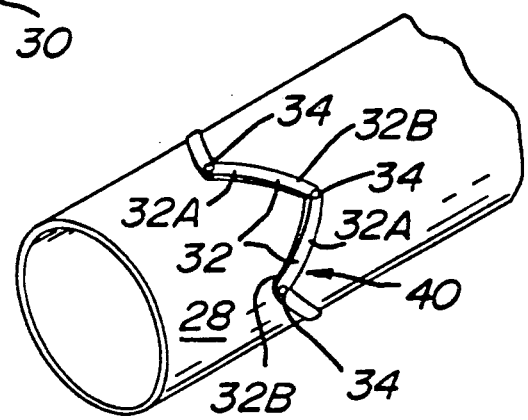
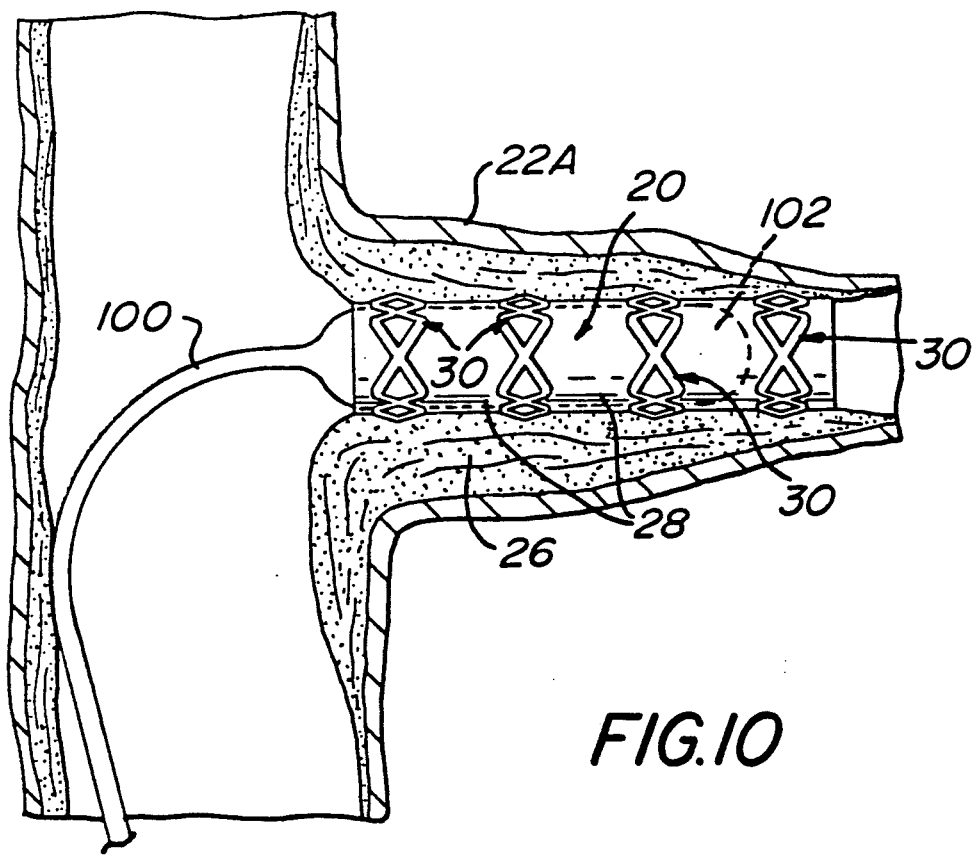

ENDOVASCULAR BYPASS GRAFT

BACKGROUND OF THE INVENTION

The invention relates generally to medical devices and methods of use in vessels, ducts or lumens of living beings, and more particularly to expandable intraluminal grafts and methods of use within the vascular tree of a living being to revascularize any blood vessel which is occluded (either partially or totally) by intrinsic or extrinsic disease.

Percutaneous balloon intraluminal dilation of vascular stenoses or blockages through the use of an angioplasty balloon catheter have proven quite successful. However, such procedures are not without risk or some drawbacks. In particular, the angioplasty balloon is inflated within the narrowed vessel in order to shear and disrupt the wall components of the vessel to obtain a large lumen. The relative incompressible plaque remains unaltered by this procedure, while the more elastic medial and adventitial layers of the body passageways stretch around the plaque. This process produces subintimal dissection, splitting, tearing, and disruption of the intact intima and wall layers. If the section forms a transverse tear it produces a flap which may lift away from the artery and may produce an obstruction to the lumen, and therefore make the blockage and stenosis worse. In addition, if there is a heavy plaque on one side of the artery wall (as occurs in 80% of atherosclerotic stenotic lesions) the thinner layer may be disrupted by the inflation of the balloon and cause hemorrhage. Moreover, after the balloon is decompressed any loose material may dislodge completely and act as an embolic source to occlude the lumen of the vessel distally to such an acute extent as to result in significant emergency ischemic conditions. This situation has occurred frequently enough to pose a significant risk to the patient.

Laser assisted balloon angioplasty has been used frequently in recent years to revascularize a totally occluded vessel. In particular the occlusion is opened with the laser and then the opening is expanded further by balloon angioplasty. One of the problems with this revascularization procedure is that the laser causes intimal damage along with the balloon. Moreover, this procedure has only been useful for short segment occlusions. When long segment occlusions are attacked by this procedure the reocclusion rate has proven to be very high, and sometimes even made worse.

In both simple balloon angioplasty and in laser assisted balloon angioplasty there is a high incidence of recurrence of the stenosis or obstruction. This is, of course, in addition to the risk of embolization and acute occlusion and disruption of the artery with massive hemorrhage. In addition, there are certain vessels bearing areas of plaque which are not amenable to balloon angioplasty because of the fact that they are orificial plaques, i.e., plaques at the orifice of a branch artery. Thus, when the balloon is inserted across this type of lesion and inflated, it inflates differentially, that is the portion of the balloon in the larger part of the artery inflates more than the portion of the balloon crossing the narrowed or stenotic segment. In fact the portion of the balloon crossing the narrowed or stenotic segment frequently does not inflate at all. Therefore, unsuccessful attempts at inflation are the rule rather than the exception. This is particularly true in attempting the revascularization of renal arteries or the superior mesenteric artery.

Intraluminal endovascular grafting has been demonstrated by experimentation to present an alternative to conventional vascular bypass surgery. Such "grafting" involves either the percutaneous insertion into a blood vessel of a tubular prosthetic graft or stent or an open insertion thereof through a short segment exposed portion of the blood vessel. The graft is typically positioned in a predetermined location within the blood vessel and then expanded by a catheter delivery system. However, the use of conventional bypass grafts exhibits the tendency of recurring stenosis. Such restenosis may progress to the point where the graft fails. In this connection the cause of stenosis in bypass grafts (including dialysis access fistulas) is usually fibro-intimal hyperplasia (also known as pseudo-intimal hyperplasia or neo-intimal hyperplasia), a very elastic fibrous tissue which recollapses almost immediately upon relaxation of the balloon. Such tissues are, however, ideal for being supported by a stent (i.e., a self supporting member).

Accordingly, it has been suggested, and there is some activity now occurring, to use stents in revascularization procedures to preclude restenosis. Another useful area of stent application is percutaneous angioplasty of Takayasu arteritis and neurofibromatosis arterial stenoses, since those conditions may show poor response and recurrance which is very high due to the fibrotic nature of these lesions.

The stent devices which have been used for the foregoing procedures have included cylindrical springs of stainless steel, sleeves of expandable heat sensitive material, and expandable sleeves formed of linked stainless steel wires arranged in a zig-zag configuration. The problems with these devices is there is no effective control over the final expanded configuration of each structure.

As will be appreciated by those skilled in the art the expansion of a coiled spring type stent is predetermined by the spring constant and the modulus of elasticity of the particular material making up the spring. These same factors predetermine the amount of expansion of the zig-zag stainless steel wire stents. In the case of an intraluminal stent formed of a heat sensitive material, which expands on heating, the amount of expansion is likewise predetermined by the heat expansion characteristics of the particular alloy utilized in the manufacture of the device. Therefore, once these expandable sleeve-like devices are inserted into the lumen their size can change. Moreover, if there has been a miscalculation in the size of the fit, an undersized stent may not expand enough to become impacted into the arterial wall for securement thereto, thus allowing it to migrate or move from the desired position and possibly even cause embolic occlusion distal to the point of insertion. An oversized graft may cause rupture of the arterial wall or tear in the plaque at the ends of the graft, producing a dissection point.

Therefore, there is an element of significant risk in the use of the prior art stent devices for revascularization of occluded arteries. Moreover, and perhaps more significantly another problem with the use of prior art devices for revascularization procedures, however, is the fact that such devices are mesh-like or otherwise open or perforated and hence susceptible to scar tissue ingrowth. Another problem with such stents is their relative rigidity. This factor requires them to be used for short occlusive lesions, since they are unable to follow the natural curves of the vessel.

Examples of various types of expandable grafts/stents are disclosed in U.S. Pat. Nos. 4,047,252 (Liebig et al), 4,503,569 (Dotter), 4,580,568 (Gianturo), 4,733,665 (Palmaz), 4,740,207 (Kreamer), 4,776,337 (Palmaz), 4,795,458 (Regan), and 4,856,516 (Hillstead), and in the following literature: "Balloon-Expandable Intracoronary Stents in the Adult Dog", Circulation, Aug. 1987, pages 450–456, Vol. 76, No. 2; "Normal and Stenotic Renal Arteries: Experimental Balloon-expandable Intraluminal Stenting", Radiology, 1987, pages 705–708, Vol. 164, No. 3; "A Titanium-Nickel Alloy Intravascular Endoprosthesis", Transactions American Society of Artificial Internal Organs, 1988, pages 399–403, Vol. XXXIV; "Self-Expanding Endovascular Stent in Experimental Atherosclerosis", Radiology, Mar. 1989, pages 773–778, Vol. 170, No. 3; "Emergency Stenting for Acute Occlusion After Coronary Balloon Angioplasty", Circulation, Nov. 1988, pages 1121–1127, Vol. 78, No. 5; "Intravascular Stents for Angioplasty", CARDIO, Dec. 1987; "Intra-Arterial Stenting in the Atherosclerotic Rabbit", Circulation, Sept. 1988, pages 646–653, Vol. 78, No. 3; "Intravascular Stents to Prevent Occlusion and Restenosis After Transluminal Angioplasty", The New England Journal of Medicine, Mar. 1987, pages 701–706, Vol. 316, No. 12; "A Polyester Intravascular Stent for Maintaining Luminal Patency", Texas Heart Institute Journal, Nov. 1, 1988, pages 12–16, Vol. 15. "Post Dilatation Stenting: Early Experience of the Use of an Endocoronary Prosthesis to Prevent Restenosis Recurrance After Angioplasty", J. Cardiovasc. Surg. 28, 1987, Session 8: CARDIAC-CORONARY (II); "Intravascular Stents to Prevent Occlusion and Restenosis After Transluminal Angioplasty", Abstract from New England Journal of Medicine 1987, Volume 316, pages 701–706; "Vascular Stenting in Normal and Atherosclerotic Rabbits", Circulation, Feb. 1990, Vol. 81, No. 2, pages 667–683; Treatment of Major Venous Obstruction with an Expandable Endoluminal Spiral Prosthesis, J. Cardiovasc. Surg. 30, 1989, pages 112–117; and Venous Stenases in Dialysis Shunts: Treatment with Self-Expanding Metallic Stents, Radiology, Feb. 1989, Vol. 170, No. 2, pages 401–405.

Accordingly, the need exists for an expandable intraluminal vascular bypass graft and methods of use which overcomes the disadvantages of the prior art, e.g., can be used over long distances, for long segment occlusions in the vascular tree, while acting to prevent acute and chronic recurrence.

OBJECTS OF THE INVENTION

It is a general object of this invention to provide an expandable intraluminal bypass graft which overcomes the disadvantages of the prior art.

It is a further object of this invention to provide an expandable intraluminal vascular bypass graft which is both flexible and formed of a material which is impervious to the ingrowth of tissue.

It is still a further object of this invention to provide an expandable intraluminal vascular bypass graft which can be used in blood vessels having long obstructions or restrictions which are to be revascularized or opened by various methods, such as lasers, borers, grinders, etc., which might have a tendency to cause intimal damage and fail if used in such long obstructions/restrictions.

It is yet a further object of this invention to provide an expandable intraluminal vascular bypass graft which can be used for revascularizing a lesion at the orifice of a branch artery in a living being.

It is yet a further object of this invention to provide methods of use of an expandable intraluminal vascular bypass graft for revascularizing arteries in living beings.

SUMMARY OF THE INVENTION

These and other objects of this invention are achieved by providing an expandable intraluminal vascular bypass graft and method of use.

The graft is arranged for introduction within a portion of a blood vessel, duct, or lumen of a living being and comprises an elongated sleeve having at least one stent mounted thereon. The sleeve is of a generally tubular shape having a longitudinal axis and formed of a first, relatively flexible material. The material is impervious to the ingrowth of tissue therein. The stent is a generally ring-like member and is mounted about the periphery of a surface, e.g., inner or outer, of the sleeve to form a first sleeve section.

The stent is arranged to be expanded from a compact state to an expanded state, as the sleeve is so expanded whereupon the internal cross-sectional area of the sleeve is enlarged. In the expanded state, the stent is resistant to contraction back to the compact state to thereby hold the sleeve in the expanded state.

The sleeve is able to bend longitudinally with respect to the longitudinal axis to enable the graft to be readily accommodated within a curved blood vessel, duct, or lumen.

In accordance with a preferred embodiment of the invention, the graft includes at least one portion that is arranged to be readily severed to facilitate the sizing of the graft for the particular length of portion of the vessel, duct or lumen into which the graft will be placed.

The method of use of the graft entails introducing it in its contracted state into a desired portion of the blood vessel, duct, or lumen by utilizing some means, e.g., disposing the sleeve on a conventional balloon catheter. With the graft in position within the desired portion of the blood vessel, duct or lumen the means for expanding the stent is operated, e.g., the balloon of the catheter inflated, to cause the stent means to expand to the expanded state. The expanding means, e.g., balloon, is then removed, e.g., withdrawn out of the expanded graft, and the graft, in its expanded state, is left permanently in place in the portion of the blood vessel, duct or lumen.

DESCRIPTION OF THE DRAWINGS

Other objects and many attendant advantages of this invention will become readily appreciated as the same becomes better understood by reference to the following detailed description when considered in connection with the accompanying drawings wherein:

FIG. 1 is a longitudinal sectional view of a stenosed artery of a living being showing one embodiment of an expandable intraluminal vascular bypass graft constructed in accordance with this invention after the graft has been expanded in place;

FIG. 2 is a longitudinal sectional view of the stenosed artery shown in FIG. 1 prior to the introduction of the graft therein;

FIG. 3 is a longitudinal sectional view of the stenosed artery shown in FIG. 1 after the introduction of the graft therein, but prior to its expansion;

FIG. 4 is a longitudinal sectional view of the stenosed artery shown in FIG. 1 during an intermediate step in the use of the graft, wherein an initial portion of the graft has been expanded by a balloon catheter;

FIG. 5 is an enlarged sectional view taken along lines 5—5 of FIG. 4;

FIG. 6 is an enlarged sectional view taken along lines 6—6 of FIG. 4;

FIG. 7 is a longitudinal sectional view of the stenosed artery shown in FIG. 1 during a later step in the use of the graft, wherein the entire graft has been expanded by the balloon catheter but prior to its withdrawal from the graft;

FIG. 8 is a perspective view of one end portion of the graft of FIG. 1 shown in its expanded state;

FIG. 9 is a perspective view of one end portion of an alternative embodiment of the graft of FIG. 1 shown in its expanded state; and FIG. 10 is a longitudinal sectional view of a stenosed side branch orifice, e.g., renal artery, of a living being showing the graft of this invention after the graft has been expanded in place.

DETAILED DESCRIPTION OF THE PREFERRED EMBODIMENTS

Referring now to various figures of the drawing where like reference numerals refer to like parts there is shown at 20 in FIG. 1 an expandable, intraluminal vascular bypass graft constructed in accordance with this invention.

The graft 20 is arranged for revascularizing lesions, e.g., atherosclerotic plaque lesions, in arteries, and is particularly useful in revascularizing long segment lesions. A typical long segment lesion is shown in FIG. 2. Thus, as can be seen therein, the segment 22 of the artery includes atherosclerotic deposits 24 forming a small or narrow, restricted passageway 26 for flow of blood therethrough. As is typically the case, such lesions are found in arterial segments, e.g., in coronary arteries which are somewhat curved. The passageway 26 may be natural or may be formed by some interventional procedure, such as will be described later.

The endovascular graft 20 is configured so that it is initially in a compact or compressed state. In that state it is arranged to be readily inserted into the arterial passageway 26 like that shown in FIG. 3. Once in position the graft is to be expanded to an expanded state. In FIG. 1 there is shown the graft expanded to a maximum expanded state, i.e., of maximum internal cross-sectional area. When the graft 20 is in the expanded state a substantially greater cross-sectional area of the arterial section is open to the free flow of blood therethrough than prior to the use of the graft 20.

As will be described in considerable detail later, the expansion of the graft 20 from the compacted state shown in FIG. 3 to the expanded state shown in FIG. 1 is preferably accomplished by a conventional balloon catheter. However, any suitable other expansion means or instrument (not shown) may be used.

Referring now to FIGS. 3–6 and 8 the details of the endovascular graft 20 will now be described. As can be seen the graft 20 basically comprises an elongated tubular member or sleeve 28 having a plurality of expandable, ring-like, stent members or sections 30 located at equaidistantly spaced positions along the longitudinal length of the member. The sleeve member 28 is formed of a thin and highly flexible material, such as expanded polytetrafloroethylene used for conventional vascular grafts. Examples of such prior art graft materials are those sold by W. C. Gore and Company under the trademark GORTEX or those sold by Impra, Inc. under the trademark IMPRAGRAFT.

The sleeve 28 is configured so that it is pleated, i.e., it includes a plurality of longitudinally extending pleats 28A. Each of the pleats extends the entire length of the graft 20. The pleated tube or sleeve 28 is normally in a compacted state as shown in FIG. 6, that is each of the pleats overlies and abuts a contiguous portion of an immediately adjacent pleat. The tube 28 is arranged to be expanded to a maximum expanded state wherein its pleats open up and form a generally continuous curved, e.g., cylindrical, surface like that shown in FIG. 5.

When the tube is in the compacted state its outside diameter is substantially less than when the tube is in the expanded state. Moreover, when the tube 28 is in its expanded state, its internal cross-sectional area is substantially greater than in the compact state. It must be pointed out at this juncture that the tube 28 may be partially expanded in an artery to be revascularized, whereupon its pleats do not fully open up (flatten out). In such a case the internal cross sectional area is less than in the fully expanded state, but more than in the compacted state, and thus still permits the freer flow of blood therethrough than would flow through passageway 26.

The spaced stent members 30 serve as a means for holding or retaining the tube 28 in any desired expanded state (i.e., from a slightly partially expanded state, not shown, to the fully expanded state like shown in FIG. 5). Thus, as can be seen, each stent member 30 basically comprises a plurality of interconnected links or struts 32. Each of the links is an elongated rigid member formed of stainless steel or some other suitable biocompatible material, e.g., tantalum, plastic. Each link has a pair of ends 32A and 32B and is joined to an associated link via a pivotable joint 34. Each joint 34 is made up of one end 32A of one link and the other end 32B of the immediately adjacent link. The link ends 32A and 32B are connected by any suitable means, e.g., a deformable member, a pin, etc., to enable the links to pivot outward with respect to each other so that the angle therebetween increases, yet which precludes the links from pivoting backward toward each other. When so arranged the links form a zig-zag pattern. In the embodiment shown herein the joint 34 comprises the material making up the links themselves, and such material is deformable, but not resilient, so that once deformed, i.e., the links pivoted outward, it doesn't return to its previous configuration.

As should be appreciated by those skilled in the art when the links 22 are pivoted outward with respect to each other the stent 30 expands from its compact state like that shown in FIG. 3 to the expanded state, with the maximum diameter expanded state being shown in FIG. 8. In accordance with a preferred aspect of this invention the joints 34 at the interfaces of each of the links of the stents are arranged to maintain any angular orientation between the connected links from the compact state to the maximum expanded state such that once the stents 30 are moved to any expanded position (whether partial or full) movement back to the compacted state is precluded.

The links of the stents of this invention serve to hold the tube member 28 in an expanded state. To that end each of the links is connected to one or more pleats 28A either externally of the sleeve (as is shown herein) or internally. Moreover, if desired the stents may be completely encased in the graft material forming the sleeve 28.

In the preferred embodiment shown in FIGS. 1-8, each of the stents 30 is made up of pairs of interconnected links to form two zig-zag patterns sharing common joints, thereby creating a diamond-like pattern stent.

In FIG. 9 there is shown an alternative graft using plural spaced stent members 40. Each stent member 40 comprises a plurality of links 32 which are interconnected via joints 34 (like that of the embodiment 30 shown in FIG. 8), except the links are not paired, so that a single zig-zag pattern is produced instead of the diamond-like pattern of FIG. 8. In all other regards the graft 20 utilizing stents 40 is the same as that described heretofore.

In order to help hold or secure the graft in position in the artery (or lumen or duct) once the graft has been expanded, the stents may include a plurality of protuberances 50 projecting slightly outward from the outer surface of the graft. These protuberances 50 act as small pressure points that help impact the graft into the arterial wall to maintain a fixed position therein. As shown in FIGS. 8 and 9, the protuberances are preferably located at the joints 34 of the various stents, but such an arrangement is exemplary and any other suitable locations may be used. Moreover, the mechanism (e.g., pivot pin, deformable member, etc.) forming the joint 34 may itself form a protuberance.

In the case of a graft 20 utilizing internally located stents, the protuberances 50 are not used. Instead the graft 20 may include a thin layer of dacron mesh (not shown) on the outer surface of the graft to impact into the vessel wall and fibrose thereat to maintain the graft in position.

Since the endovascular graft 20 of this invention is preferably formed of a flexible material, e.g., conventional vascular graft material, it can be readily bent. The use of the expansion holding stents doesn't detract from the ability of the graft to flex or bend since each stent only extends for a small portion that vary from less than one mm. to several millimeters depending on the diameter of the graft to be supported. The distance between supporting stents may vary from 3 mm to 2 cm., depending on the diameter of the graft being utilized. The graft portions between the stents enable the graft to bend or flex thereat so that the graft can assume an arcuate, undulating or otherwise bent shape with respect to its longitudinal axis.

Moreover, since the stents are spaced apart and do not extend continuously along the length of the graft 20 the graft can be easily sized to whatever length vascular segment is desired to be revascularized. To that end, all that is required is to sever a length of the graft 20 at any particular point between two immediately adjacent stents 30 to produce a custom length graft.

Use of the graft 20 will now be described with reference to FIGS. 1-7. The graft 20, in its compacted state as shown in FIG. 3, is inserted by any suitable procedure or instrument, e.g., on a conventional balloon catheter 100, into the passageway 26 extending through the artery segment to be revascularized. Once in position the balloon 102 at the distal end of the catheter 100 is inflated to cause it to expand outward radially. This action causes the linear pleats 28A of the sleeve portion 28 of the device 20 to begin to flatten out and at the same time causes the links 32 of the stent members 30 located over the balloon 102 to pivot outward about their joints. The means forming the joints 34, being resistant to permitting the links to pivot back toward each other, holds the portion of the graft which has been expanded in that expanded state.

If the graft section is longer than the balloon, e.g., 10 cm or more in length, the balloon is initially positioned so that it is in the end of the graft furthest from the entrance point in the artery (i.e., in the distal end of the graft) the balloon is then deflated and moved longitudinally down the interior of the graft 20 in the proximal direction to the next contiguous unexpanded section of the graft. The balloon 102 is then reinflated to expand that contiguous section of the graft 20. This expansion sequence continues until the entire length of the device 20 is expanded.

It must be pointed out at this juncture that in the drawings the graft 20 is shown expanded to a maximum diameter along its entire length. That is merely exemplary. Thus, in some revascularization procedures different sections of the graft 20 may be expanded to different diameters.

With short segment arteries the graft 20 is utilized by inserting an intraluminal balloon catheter 100 within the graft 20 and then introducing that combination into the artery until the graft is positioned at the desired location within a vessel segment. The balloon 102 is then expanded, thereby expanding the entire length of the graft 20 at one time to the desired degree of expansion. The balloon is then deflated and the catheter withdrawn. The graft 20 then maintains its position within the artery at that location in the same manner as when used in long arterial segments.

Referring now to FIG. 10, the use of a graft 20 for revascularizing an orificial or branch, e.g., renal, artery will now be described. As mentioned earlier heretofore, the revascularization of such orificial branches through ballooning techniques has not been as successful as desired due to the differential expansion of the balloon. However, use of the subject graft 20 obviates that problem since the graft constrains the balloon 102 along its length so that it is precluded from expanding differentially. Instead, the balloon expands equally throughout its length. Accordingly, the graft 20 of the subject invention allows one to cross the branch lesion, inflate the balloon with the graft in place, and then deflate and extract the balloon leaving the graft in position holding the orificial lumen open.

As should be appreciated from the foregoing, one significant advantage of the graft 20 of the subject invention is that with the inflation of the balloon, should disruption of the blood vessel wall occur, it will be immediately sealed by the graft 20, thus preventing hemorrhage. A further advantage of the graft 20 is that it does not produce a portal for ingrowth of neointima or pseudointimal hyperplasia to occlude the graft body. While there may be some ingrowth into the wall of the member 28, such growth does not extend through the wall into the interior of the graft. Thus, the subject graft reduces the chance of recurrent stenosis or occlusion from a fibrous response in the blood vessel. Still another advantage of the graft 20 is that long lengths of occlusions can be opened by conventional instrument means, such as lasers, grinders, etc., which may leave a long, highly thrombogenic surface that precludes long patency. Thus, even though such a thrombogenic surface may be created by such conventional instruments, that surface is made non-thrombogenic by the use of the graft 20. This action will obviously increase the long-term graft patency. Yet another advantage of the subject graft is that it can be inserted without major surgery, either through a local arteriotomy under radiographic control, or through percutaneous blood vessel catheterization.

The stenting function provided by the spaced stents 30 or 40 reinforces the body passageway producing a lumen, which, though flexible, is not collapsible. In particular, the wall of the graft is supported about its length by the various spaced stents either externally or internally to maintain internal lumen diameter.

Still other advantages of the graft 20 are that it can be pre-fabricated in variable lengths so that after measurement radiographically an appropriate length and diameter of graft 20 can be chosen to befit the vessel and the length of the occlusive lesion appropriate to that patient. This foregoes the necessity of multiple insertions of small, short, intraluminal devices that are present available. Such action reduces the chance of intimal damage, embolization distally, and in addition improves placement during the process of balloon dilation.

Without further elaboration the foregoing will su fully illustrate my invention that others may, by applying current or future knowledge, adopt the same for use under various conditions of service.

I claim:

1. An intraluminal graft for introduction within a portion of a blood vessel, duct or lumen of a living being, said graft comprising a sleeve and at least two stent means mounted thereon, said sleeve being an elongated member of a generally tubular shape having a longitudinal axis and formed of a first, relatively flexible, material, said material being impervious to the ingrowth of tissue therein, each of said stent means being generally ring-like in shape, aid stent means being mounted about the periphery of a surface of said sleeve at selected points therealong to form (a) respective first sleeve sections, each of said first sleeve sections extending for respective portions of the length of said sleeve and being spaced from each other, said sleeve additionally comprising at least one second section, said second section being interposed between said at least two first sections, each of said stent means being arranged to be expanded from a compact state to an expanded state as said sleeve is so expanded so that the cross-section area of the interior of said sleeve is enlarged, said stent means when in said expanded state being resistant to contraction back to said compact state to thereby hold said sleeve in said expanded state, said graft being able to bend longitudinally with respect to said axis to enable said graft to be readily accommodated within a curved blood vessel, duct or lumen.

2. The graft of claim 1 wherein each of said ring-like members comprises a plurality of interconnected movable links.

3. The graft of claim 2 wherein said sleeve comprises a plurality of longitudinally extending pleats when said sleeve is in said compact state.

4. The graft of claim 3 wherein said sleeve comprises an outer peripheral surface and wherein each of said stent means is mounted on said outer peripheral surface.

5. The graft of claim 3 wherein said links are arranged in either diamond-like shaped configurations or in zig-zag shaped configurations.

6. The graft of claim 2 wherein said links are arranged in either diamond-like shaped configurations or in zig-zap shaped configurations.

7. The graft of claim 1 wherein said sleeve comprises a plurality of longitudinally extending pleats when said sleeve is in said compact state.

8. The graft of claim 7 wherein said sleeve comprises an outer peripheral surface and wherein each of said stent means is mounted on said outer peripheral surface.

9. The graft of claim 1 wherein said sleeve is arranged to be served at any of said second sections to tailor the length of said graft to the length of the vessel, duct or lumen portion.

10. The graft of claim 9 wherein each of said stent means comprises a generally ring-like member having a plurality of interconnected movable links.

11. The graft of claim 10 wherein said sleeve comprises an outer peripheral surface and wherein stent means is mounted on said outer peripheral surface.

12. The graft of claim 11 wherein said links are arranged in either diamond-like shaped configurations or in zig-zag shaped configurations.

13. The graft of claim 12 wherein said sleeve comprises a plurality of longitudinally extending pleats when said sleeve is in said compact state.

14. An intraluminal graft for introduction within a portion of a blood vessel, duct or lumen of a living being, said graft comprising a sleeve and stent means mounted thereon, said sleeve being an elongated member of a generally tubular shape having a longitudinal axis and formed of a first, relatively flexible, material, said material being impervious to the ingrowth of tissue therein, said sleeve comprising an outer peripheral surface, and stent means being generally ring-like in shape and mounted on said outer peripheral surface of said sleeve to form a first sleeve section, said stent means being arranged to be expanded from a compact state to an expanded state as said sleeve is so expanded so that the cross-sectional area of the interior of said sleeve is enlarged, said stent means when in said expanded state being resistant to contraction back to said compact state to thereby hold said sleeve in said expanded state, said graft being able to bend longitudinally with respect to said axis to enable said graft to be readily accommodated within a curved blood vessel, duct or lumen.

15. An intraluminal graft for introduction within a portion of a blood vessel, duct or lumen of a living being, said graft comprising a sleeve and stent means mounted thereon, said sleeve being an elongated member of a generally tubular shape having a longitudinal axis, an outer peripheral surface, and being formed of a first, relatively flexible, material, said material being impervious to the ingrowth of tissue therein, said stent means being generally ring-like in shape and mounted on said outer peripheral surface of said sleeve to form a first sleeve section, said first sleeve section extending for only a portion of the length of said sleeve, said sleeve additionally comprising a second sleeve section contiguous with said first sleeve section, said stent means being arranged to be expanded from a compact state to an expanded state as said sleeve is so expanded so that the cross-sectional area of the interior of said sleeve is enlarged, said stent means when in said expanded state being resistant to contraction back to said compact state to thereby hold said sleeve in said expanded state, said first and second sleeve sections being able to bend longitudinally with respect to said axis to enable said graft to be readily accommodated within a curved blood vessel, duct or lumen.

16. A method for implanting an intraluminal graft within a portion of a blood vessel, duct, or lumen of a living being, said graft comprising a sleeve and at least two stent means mounted thereon, said sleeve being an elongated member of a generally tubular shape having a longitudinal axis and formed of a first, relatively flexible, material, said material being impervious to the ingrowth of tissue therein, each of said stent means being generally ring-like in shape, said stent means being mounted about the periphery of a surface of said sleeve at selected points therealong to form respective first sleeve sections, each of said first sleeve sections extending for respective portions of the length of said sleeve and being spaced from each other, said sleeve additionally comprising at least one second section, said second section being interposed between said at least two first sections, each of said stent means being arranged to be expanded from a compact state to a expanded state as said sleeve is so expanded so that the cross-sectional area of the interior of said sleeve is enlarged, said stent means when in said expanded state being resistant to contraction back to said compact state to thereby hold said sleeve in said expanded state, said graft being able to bend with respect to said axis to enable said graft to be readily accommodated within a curved blood vessel, duct, or lumen, said method comprising introducing said graft in said compact state into said portion of said blood vessel, duct, or lumen and thereafter utilizing some means to cause said stent means and said sleeve to expand to said expanded state, and leaving said graft in said position in said expanded state.

17. The method of claim 16 additionally comprising severing said graft at any of said second sections to tailor the length of said graft to the length of the blood vessel, duct, or lumen portion prior to introduction therein.

18. The method of claim 16 wherein said stent means are expanded by a catheter.

19. The method of claim 18 wherein said catheter is a balloon catheter.

20. The method of claim 19 wherein said vessel, duct, or lumen comprises a branch artery having an orificial lesion therein, said graft being disposed within a passageway in said lesion and expanded therein by said balloon catheter.

21. The method of claim 18 additionally comprising expanding said plural stent means sequentially by use of said catheter.

22. A method for implanting an intraluminal graft within a portion of a blood vessel, duct, or lumen of a living being, said graft comprising a sleeve and stent means mounted thereon, said sleeve being an elongated member of a generally tubular shape having a longitudinal axis and formed of a first, relatively flexible, material, said material being impervious to the length of tissue therein, said stent means being generally ring-like in shape and mounted about the periphery of a surface of said sleeve to form a first sleeve section, said stent means being arranged to be expanded from a compact state to an expanded state as said sleeve is so expanded so that the cross-sectional area of the interior of said sleeve is enlarged, said stent means when in said expanded state being resistant to contraction back to said compact state to thereby hold said sleeve in said expanded state, said graft being able to bend with respect to said axis to enable said graft to be readily accommodated within a curved blood vessel, duct, or lumen, said method comprising introducing said graft in said compact state into said portion of said blood vessel, duct, or lumen by a catheter, said graft being disposed on said catheter prior to introduction into said portion of said blood vessel, duct, or lumen, said catheter being used to expand said stent means to said expanded state and said catheter is then removed from said graft leaving said graft in said position in said expanded state.

23. The method of claim 22 wherein said catheter is a balloon catheter.

24. The method of claim 23 wherein said vessel, duct, or lumen comprises a branch artery having an orificial lesion therein, said graft being disposed within a passageway in said lesion and expanded therein by said balloon catheter.

25. A method for implanting an intraluminal graft within a portion of a blood vessel, duct, or lumen of a living being, said graft comprising a sleeve and plural stent means mounted thereon, said sleeve being an elongated member of a generally tubular shape having a longitudinal axis and formed of a first, relatively flexible, material and comprising plural first and second sections, said material being impervious to the ingrowth of tissue therein, each of said stent means being generally ring-like in shape and mounted about the periphery of a surface of said sleeve at selected points therealong to form respective ones of first sleeve sections, each of said sleeve sections extending for respective portions of the length of said sleeve and being spaced from one another, said second sleeve sections being interposed between said first sleeve sections, said stent means being arranged to be expanded from a compact state to an expanded state as said sleeve is so expanded so that the cross-sectional area of the interior of said sleeve is enlarged, said stent means when in said expanded state being resistant to contraction back to said compact state to thereby hold said sleeve in said expanded state, said graft being able to bend with respect to said axis to enable said graft to be readily accommodated within a curved blood vessel, duct, or lumen, said method comprising introducing said graft in said compact state into said portion of said blood vessel, duct, or lumen by a catheter, said graft being disposed on said catheter prior to introduction into said portion of said blood vessel, duct or lumen, said catheter being used to expand said plural stent means sequentially to said expanded state and said catheter is then removed from said graft leaving said graft in said position in said expanded state.

26. The method of claim 25 wherein said catheter is a balloon catheter.

27. The method of claim 26 wherein said balloon catheter is inflated to expand at least a first one of said stent means to said expanded state, whereupon said balloon catheter is deflated and withdrawn from said expanded portion of said sleeve into another portion thereof and is then reinflated to expand at least a second of said stent means to said expanded state.

28. A method for implanting an intraluminal graft within a portion of a blood vessel, duct, or lumen of a living being, said graft comprising a sleeve and plural stent means mounted thereon, said sleeve being an elongated member of a generally tubular shape having a longitudinal axis and formed of a first, relatively, flexible, material and comprising plural first and second sections, said material being impervious to the ingrowth of tissue therein, each of said stent means being generally ring-like in shape and mounted about the periphery of a surface of said sleeve at selected points therealong to form respective ones of first sleeve sections, each of said sleeve sections extending for respective portions of the length of said sleeve and being spaced from one another, said second sleeve sections being interposed between said first sleeve sections, said stent means being arranged to be expanded from a compact state to an expanded state as said sleeve is so expanded so that the cross-sectional area of the interior of said sleeve is enlarged, said stent means when in said expanded state being resistant to contraction back to said compact state to thereby hold said sleeve in said expanded state, said graft being able to bend with respect to said axis to enable said graft to be readily accommodated within a curved blood vessel, duct, or lumen, said method comprising severing said graft at any of said second sections to tailor the length of said graft to the length of the blood vessel, duct or lumen portion prior to introduction therein, introducing said graft in said compact state into said portion of said blood vessel, duct, or lumen by a catheter, expanding said plural stent means sequentially by use of said catheter and leaving said graft in said position in said expanded state.

29. The method of claim 28 wherein said graft is disposed on said catheter prior to introduction into said portion of said blood vessel, duct, or lumen, and is introduced into said portion by means of said catheter, whereupon said catheter is used to expand said stent means to said expanded state and said catheter is then removed from said graft.

30. The method of claim 29 wherein said catheter is a balloon catheter.

31. The method of claim 30 wherein said balloon catheter is inflated to expand at least a first one of said stent means to said expanded state, whereupon said balloon catheter is deflated and withdrawn from said expanded portion of said sleeve into another portion thereof and is then reinflated to expand at least a second of said stent means to said expanded state.

* * * * *